(12) United States Patent
Hsieh et al.

(10) Patent No.: US 7,031,425 B2
(45) Date of Patent: Apr. 18, 2006

(54) METHODS AND APPARATUS FOR GENERATING CT SCOUT IMAGES

(75) Inventors: Jiang Hsieh, Brookfield, WI (US); Robert F. Senzig, Germantown, WI (US); Priya Gopinath, North Arlington, NJ (US); Kelly Lynn Karau, New Berlin, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 182 days.

(21) Appl. No.: 10/306,053

(22) Filed: Nov. 27, 2002

(65) Prior Publication Data

US 2004/0101087 A1 May 27, 2004

(51) Int. Cl.
*G01N 23/087* (2006.01)
(52) U.S. Cl. .................................... 378/5; 378/98.11
(58) Field of Classification Search ............... 378/5, 378/41, 42, 53, 54, 98.9, 98.11, 16
See application file for complete search history.

(56) References Cited

U.S. PATENT DOCUMENTS

| 4,174,481 | A | * | 11/1979 | Liebetruth | .................... 378/20 |
|---|---|---|---|---|---|
| 4,247,774 | A | * | 1/1981 | Brooks | ........................ 250/367 |
| 4,361,901 | A | | 11/1982 | Daniels et al. | |
| 4,686,695 | A | * | 8/1987 | Macovski | .................... 378/146 |
| RE32,961 | E | * | 6/1989 | Wagner | ........................ 378/4 |
| 5,305,363 | A | * | 4/1994 | Burke et al. | .................... 378/4 |
| 5,400,378 | A | * | 3/1995 | Toth | ............................ 378/16 |
| 5,570,403 | A | * | 10/1996 | Yamazaki et al. | ............. 378/5 |
| 5,665,971 | A | | 9/1997 | Chen et al. | |
| 6,018,562 | A | | 1/2000 | Willson | |
| 6,185,272 | B1 | | 2/2001 | Hiraoglu et al. | |
| 6,236,709 | B1 | | 5/2001 | Perry et al. | |
| 6,320,931 | B1 | | 11/2001 | Arnold | |
| 6,369,389 | B1 | | 4/2002 | Berlad et al. | |
| 6,501,819 | B1 | * | 12/2002 | Unger et al. | .................... 378/5 |
| 6,507,633 | B1 | | 1/2003 | Elbakri et al. | |
| 6,560,315 | B1 | | 5/2003 | Price et al. | |
| 6,816,564 | B1 | * | 11/2004 | Charles et al. | .................. 378/5 |
| 6,816,571 | B1 | * | 11/2004 | Bijjani et al. | ................. 378/57 |
| 6,914,959 | B1 | * | 7/2005 | Bailey et al. | ................. 378/65 |
| 2002/0163988 | A1 | * | 11/2002 | Nisius et al. | ................ 376/245 |
| 2003/0063787 | A1 | | 4/2003 | Natanzon et al. | |

\* cited by examiner

*Primary Examiner*—Edward J. Glick
*Assistant Examiner*—Thomas R Artman
(74) *Attorney, Agent, or Firm*—Carl B. Horton, Esq.; Armstrong Teasdale LLP

(57) ABSTRACT

A method for obtaining data includes acquiring Computed Tomography (CT) scout data at a Z location with a first x-ray spectrum, and acquiring CT scout data at the Z with a second x-ray spectrum different from the first x-ray spectrum.

21 Claims, 2 Drawing Sheets

Illustration of kV settings as a function of sampling

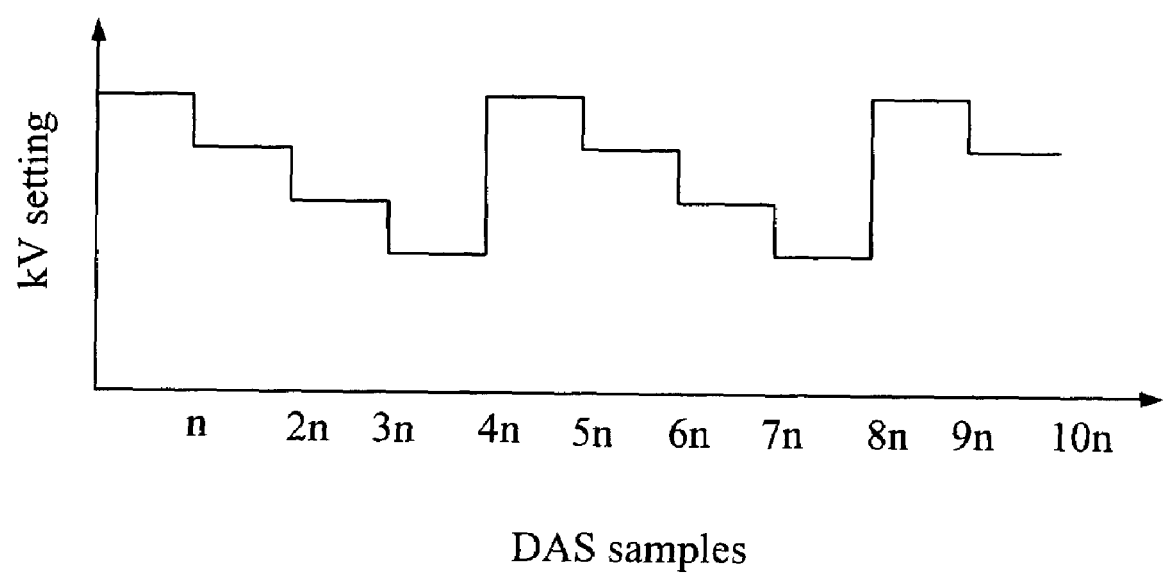
Fig. 3 Illustration of kV settings as a function of sampling

METHODS AND APPARATUS FOR GENERATING CT SCOUT IMAGES

BACKGROUND OF THE INVENTION

This invention relates to computed tomographic (CT) imaging, and more particularly to methods and apparatus for obtaining data and for generating CT scout images using a mechanical CT scanner.

Many organs of a body, such as, for example, kidneys do not lie in the conventional sagittal, coronal, or axial planes of the body. Such organs are best viewed in an angle between the coronal and sagittal views. Tomosynthesis is one technique that allows a radiologist to view individual planes of an organ of interest, potentially reducing the problem of superimposed structures that may limit conventional techniques. Tomosynthesis carried out on known X-ray systems over a limited set of views can provide the radiologist with a stereoscopic view of the object with a feel for the depth. However, three-dimensional (3D) structures are currently limited in that they are viewed mostly as two-dimensional structures on the X-ray films. Accordingly, the methods and apparatus described herein address the detection and diagnosis of three-dimensional structures by obtaining data and generating CT scout images, as known as scanogram.

BRIEF DESCRIPTION OF THE INVENTION

In one aspect, a method for obtaining data is provided. The method includes acquiring Computed Tomography (CT) scout data at a Z location with a first x-ray spectrum, and acquiring CT scout data at the Z location with a second x-ray spectrum different from the first x-ray spectrum.

In another aspect, a multi energy imaging system is provided. The system includes a radiation source, a radiation detector, and a computer operationally coupled to the radiation source and the radiation detector. The computer is configured to acquire Computed Tomography (CT) scout data from the radiation detector at a Z location with a first x-ray spectrum, and acquire CT scout data at the Z location from the radiation detector with a second X-ray spectrum different from the first x-ray spectrum.

In another aspect, a mechanical CT system is provided. The system includes a rotatable gantry, a x-ray source mounted on the gantry, a x-ray detector mounted on the gantry substantially opposite the source, and a computer operationally coupled to the gantry, the source, and the detector. The computer is configured to acquire Computed Tomography (CT) scout data from the x-ray detector at a Z location with a first x-ray spectrum, and acquire CT scout data at the Z location from the x-ray detector with a second x-ray spectrum different from the first x-ray spectrum.

In yet another aspect, a processor is configured to receive Computed Tomography (CT) scout data regarding a first x-ray spectrum at a Z location, and CT scout data regarding a second x-ray spectrum different from the first x-ray spectrum at the Z location.

In still another aspect, A computer readable medium encoded with a program configured to instruct a computer to acquire Computed Tomography (CT) scout data from a x-ray detector at a Z location with a first x-ray spectrum, and acquire CT scout data at the Z location from the x-ray detector with a second x-ray spectrum different from the first x-ray spectrum.

BRIEF DESCRIPTION OF THE DRAWINGS

FIG. 3 is an example of energy variation as a function of sample.

DETAILED DESCRIPTION OF THE INVENTION

Figure 1:
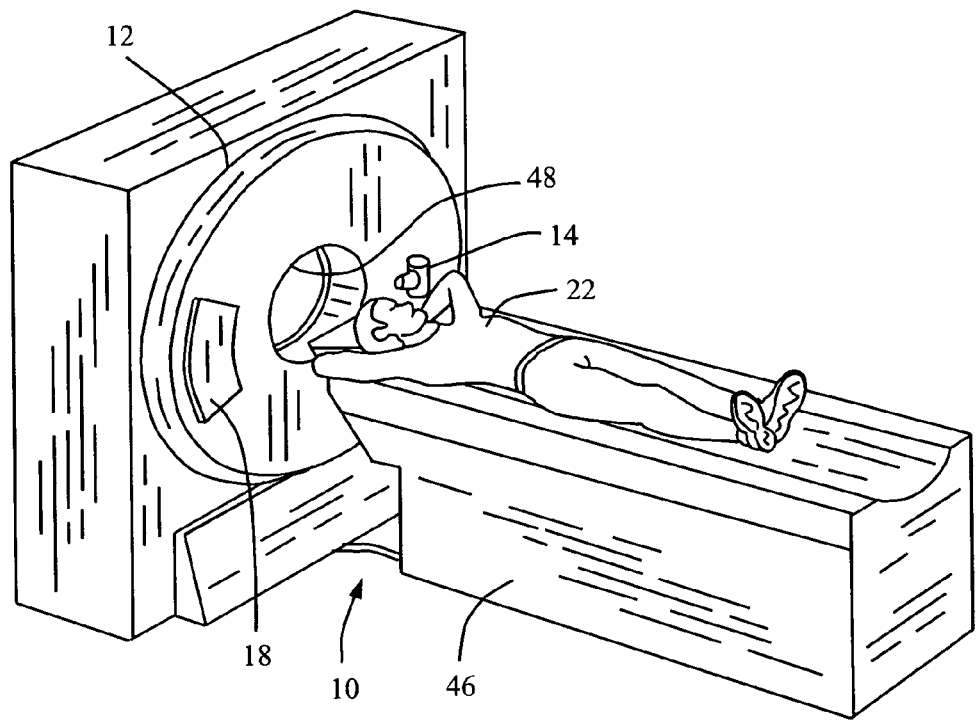
FIG. 1 is a pictorial view of a MECT imaging system.

The methods and apparatus described herein address the detection and diagnosis of 3D structures in scout images by employing novel approaches that make use of basic properties of the x-ray and material interaction. For each ray trajectory, multiple measurements with different mean x-ray energies are acquired. As explained in greater detail below, when Basis Material Decomposition (BMD) and Compton and photoelectric decomposition are performed on these measurements, additional information is obtained that enables improved accuracy and characterization. The Multienergy-Stereoscopic views as herein provided provides radiologists with not only 3D depth information but also tissue differentiation information all in a single exam.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units" (HU), which are used to control the brightness of a corresponding pixel on a cathode ray tube display.

In a scout scan or scanogram acquisition, the x-ray tube and detector remains stationary throughout the scan. The patient is indexed at a constant speed while x-rays are emitted forming a fan shaped x-ray beam. The data are collected by the detector and pre-processing steps are taken to convert the raw data to represent line integrals of the object attenuation coefficients. The pre-processed data is further processed with computer enhancement techniques to produce a two-dimensional image with similar appearance as a conventional radiograph. Traditionally, scout scans are used mainly as a localizer for CT scan prescription. Based on the processed scout image, an operator can determine the anatomical regions for subsequent CT scans. In typical CT examination, either A–P (tube located at 12 or 6 o'clock position) or lateral (tube located at 3 or 9 o'clock position) are acquired. As used herein, the terms CT scout scan and CT scout data broadly refers to all data acquisitions and the data acquired wherein the gantry is stationary and the table is moved including, for example, but not limited to, CT scout scans as know in the art as well as digitally reconstructed radiograph (DRR) acquisitions typically employed in radiation treatment (RT) planning.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Herein are described methods and apparatus for detecting 3D structures using a energy-discriminating (also known as multi-energy) computed tomographic (MECT) system 10 to generate scout images. First described is MECT system 10 and followed by scout applications using MECT system 10.

Energy Discrimination (Multi-Energy) CT System 10

Figure 2:
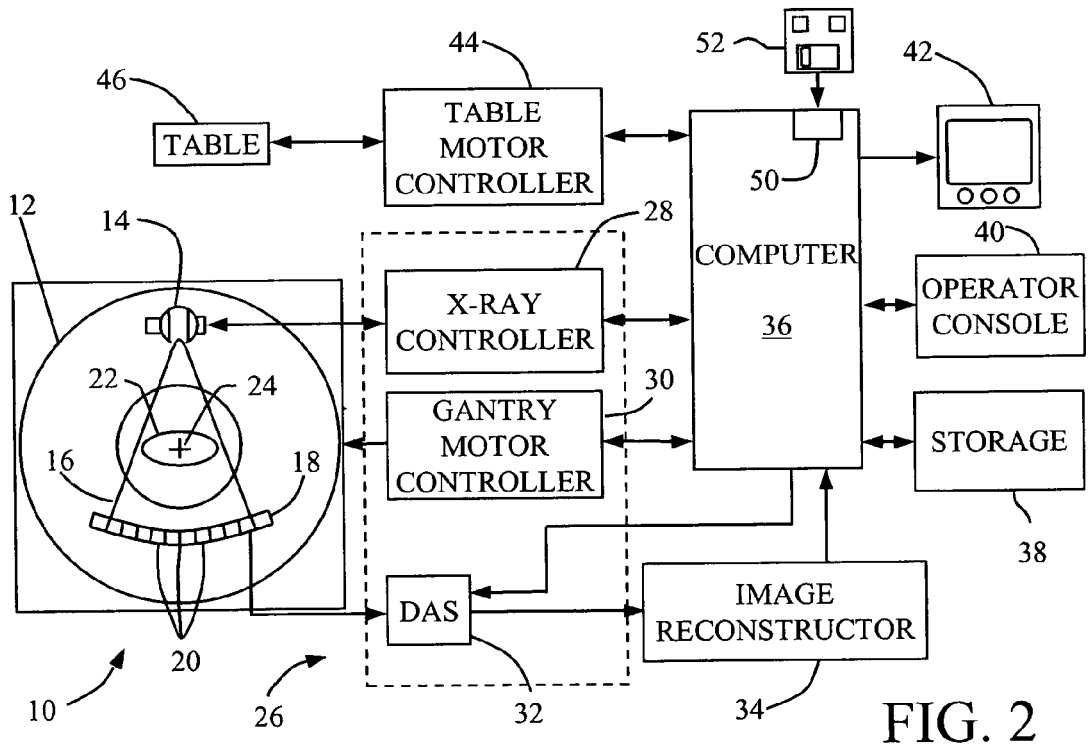
FIG. 2 is a block schematic diagram of the system illustrated in FIG. 1.

Referring to FIGS. 1 and 2, a Multi Energy multi-slice scanning imaging system, for example, a Multi Energy computed tomography (MECT) imaging system 10, is shown as including a gantry 12 representative of a "third generation" CT imaging system. Gantry 12 has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22. Each detector element 20 produces an electrical signal that represents the intensity of an impinging x-ray beam and hence the attenuation of the beam as it passes through object or patient 22. During a non-scout CT scan (e.g., a helical scan) to acquire x-ray projection data, gantry 12 and the components mounted thereon rotate about a center of rotation 24. During a scout scan, gantry 12 is held stationary at a particular scout angle while table 46 is moved in the Z direction. For a multi-energy scout scan, scouts at a particular Z location are obtained with different x-ray spectra. For a multi-energy stereoscopic view, multiple multi-energy scout scans are obtained at different scout angles. FIG. 2 shows only a single row of detector elements 20 (i.e., a detector row). However, multislice detector array 18 includes a plurality of parallel detector rows of detector elements 20 such that projection data corresponding to a plurality of quasiparallel or parallel slices can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs scout image generation. The generation steps include pre-process of the sampled data, additional enhancement of the data, and basic material decomposition.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computerreadable medium 52, such as a floppy disk or CD-ROM. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. CT imaging system 10 is an energy-discriminating (also known as multi-energy) computed tomographic (MECT) system in that system 10 is configured to be responsive to different x-ray spectra. This can be accomplished with a conventional third generation CT system to acquire projections sequentially at different x-ray tube potentials. For example, two scans are acquired either back to back or interleaved in which the tube operates at 80 kVp and 160 kVp potentials. In an exemplary embodiment, with "d" representing the detector aperture in mm, "t" representing the table translation speed in mm/s, and "s" representing the DAS sampling rate in Hz, the sampling rate is determined to be: s=t/d. The x-ray tube potentials alternate between 80 kVp and 160 kVp at the same rate. This enables the same z location to be sampled by two different potentials when two detector rows are used in the data collection. Alternatively, special filters are placed between the x-ray source and the detector such that different detector rows collect projections of different x-ray energy spectrum. Yet another embodiment is to use energy sensitive detectors such that each x-ray photon reaching the detector is recorded with its photon energy. CT system 10 is capable of performing conventional scans as in known in the art as well as the herein described Multi-Energy Scout Scans wherein during scout acquisition, mechanical CT X-ray tube 14 and detector 18 stays stationary while table 46 advances and covers the entire Z extent as desired.

Additionally, multiple angles of scout acquisition for every kV used are obtained for a given detector row as well. In other words, before moving to detector row 2n with another ray of a different Xray energy, the scout scan is taken at about 20–21 angles of rotation because it is believed that Xray takes about 21 views. Thus at the end of scanning an area of interest, there is enough data for the physician to not only see a stereoscopic view of the area but also stereoscopic views of any given tissue composition: i.e. stereoscopic view of soft tissue versus stereoscopic view of the bone etc. Alternatively, when a distributed x-ray source is employed, scouts of different projection angles can be acquired without the gantry rotation. In this configuration, different kV settings can be distributed to different projection angles. For example, if four detector rows are used for the data acquisition, two different kV settings are selected. Additionally, and still referring to the four detector row and two different Kv settings example, a plurality (X number) of different projection angles are selected. The number of projection angles are determined depending upon the organ of interest and its depth. In one embodiment, this is computed by system 10 before the scan is taken.

In another embodiment, the gantry is rotating at a constant speed while the patient is indexed. The x-ray tube is pulsed such that x-ray photons are emitted at only discrete set of angles (e.g., 20 angles). The tube voltage is adjusted from rotation to rotation. Since the patient table is indexed at a designed speed, the same z location is sampled by different detector rows at different x-ray energy.

Energy Discrimination CT (MECT) can lessen or eliminate the problems associated with conventional CT (lack of energy discrimination and material characterization) altogether. In the absence of object scatter, one only need system 10 to separately detect two regions of photon energy spectrum: the low-energy and the high-energy portions of the incident x-ray spectrum. The behavior at any other energy can be derived based on the signal from the two energy regions. This phenomenon is driven by the fundamental fact that in the energy region where medical CT is interested, two physical processes dominate the x-ray attenuation (1) Compton scatter and (2) the Photoelectric effect. In order to characterize the behavior of an object under x-ray attenuation, one only need to measure two independent parameters. Thus, detected signals from two energy regions provide enough information that we can use to resolve the energy dependence of the object being imaged.

The data analysis used in MECT includes (1) Compton and photoelectric decomposition:
   Instead of obtaining an overall attenuation coefficient as in conventional CT images, a pair of images is obtained with MECT 10, separately presenting attenuations from Compton and photoelectric processes. Also, a slight modification can result in images representing effective Z and density.

(2) Basis material decomposition (BMD):
   This method is based on the concept that the x-ray attenuation (in the energy region for medical CT) of any given material can be represented by proper density mix of other two given materials. These two materials are called the Basis Material. Through BMD, two CT images can be obtained, each presenting the equivalent density of one of the basis materials. Since density is independent of x-ray photon energy, these images are naturally free of beam hardening artifacts. Meanwhile, one has the choice: of choosing the basis material to target certain material of interest, thus enhancing the image contrast.

It should be noted that in order to optimize a dual energy CT system, the larger the spectra separation, the better the image quality. Also, the photon statistics in these two energy regions needs to be similar, otherwise, the poor statistical region will dominate the image noise.

There are different methods to obtain dual energy measurements. (1) Scan with two distinctive energy spectra. (2) Detect photon energy according to penetration depth at the detector. (3) Photon-counting. Photon counting provides clean spectra separation and adjustable energy separation point for balancing photon statistics.

Scout Applications of Energy Discriminating using Multi-energy CT System 10

The present invention applies the above principles to scout applications. In specific, MECT system 10 is configured to produce CT images in accordance with the herein described methods.

FIG. 3 illustrates an energy graph wherein four different kV settings are acquired for each z location. Once the data of multiple energies is acquired, standard techniques for material decomposition is used to either remove certain classes of objects (e.g., bones), or enhance the appearance of certain classes (e.g., contrast). Additionally, this process can be repeated for different scout angles if desired. Alternatively, this process is done at a single scout angle.

Additionally, in another alternative embodiment, employing a distributed x-ray source, scouts of multiple projection angles are acquired without rotation of gantry 12, because by utilizing a distributed x-ray source, different kV settings are distributable to different projection angles. For example, using four detector rows of array 18 for the data acquisition, two different kV settings and two different projection angles are selectable. In other words, the distributed x-ray source has different portions and a first portion of the x-ray source is energized such that a first x-ray spectrum is emitted by the first portion, and a second portion of the x-ray source is energized such that a second x-ray spectrum different from the first spectrum is emitted by the second portion.

Thus, any given Z location, is covered by multiple energies as well as from different angles of acquisition. Also, Multiple Stereoscopic views are obtainable to see soft tissue/bone/calcified tissue. And difference images are computable between multiple energies to better illustrate targeted structures at different angles through a stereoscopic view. The difference images may aid a medical practitioner such as a radiologist in understanding the nature of a pathology. For example, if a lung nodule is present in a scanned patient wherein the lung nodule is 4 mm in width and 3 mm in depth with a calcified core, the Multienergy stereoscopic view provides the radiologist not only as to the dimensions of the nodule but also the composition of the nodule (i.e., the calcified core). Post processing for stereoscopic views is different from a regular CT where the information is back projected to obtain axial images first and then 3D rendered forms. Therefore, system 10 employs software which automatically combines the scout projection data through a set of different algorithms and synthesizes images that look like conventional linear tomograms, with slices available at any depth or plane within the patient. Additionally, regular oblique scanned projection radiographs can also be used solely to provide the practitioner with different views of the organ of interest.

While the invention has been described in terms of various specific embodiments, those skilled in the art will recognize that the invention can be practiced with modification within the spirit and scope of the claims.

What is claimed is:

1. A method for obtaining data, said method comprising:
   operating a Computed Tomography (CT) imaging system comprising a detector array having a plurality of detector rows to acquire scout data at a Z location with a first x-ray spectrum;
   operating the CT imaging system to acquire scout data at the Z location with a second x-ray spectrum different from the first x-ray spectrum; and performing a basis material decomposition on the acquired scout data from the first x-ray spectrum and the second x-ray spectrum;

wherein the scout data acquired with the first x-ray spectrum and the scout data acquired with the second x-ray spectrum are acquired interleaved by different rows of the detector and further wherein said acquiring scout data at a Z location with a first x-ray spectrum comprises acquiring scout data at a first angle at a Z location with a first x-ray spectrum, said acquiring scout data at the Z location with a second x-ray spectrum different from the first x-ray spectrum comprises acquiring scout data at the first angle at the Z location with a second x-ray spectrum different from the first x-ray spectrum, said method further comprising:

acquiring scout data at a second angle at the Z location with a first x-ray spectrum;

acquiring scout data at the second angle at the Z location with a second x-ray spectrum different from the first x-ray spectrum;

generating a first difference image from the acquired scout data from the first x-ray spectrum and the second x-ray spectrum at the first angle;

generating a second difference image from the acquired scout data from the first x-ray spectrum and the second x-ray spectrum at the second angle; and generating a stereoscopic view using the first and second difference images.

2. A method in accordance with claim 1 wherein said acquiring scout data at a second angle at the Z location with a first x-ray spectrum comprises acquiring scout data at a second angle at the Z location with a first x-ray spectrum by rotating a gantry of an imaging system.

3. A method in accordance with claim 1 wherein said acquiring scout data at a second angle at the Z location with a first x-ray spectrum comprises acquiring scout data at a second angle at the Z location with a first x-ray spectrum by using a distributed x-ray source such that a gantry of an imaging system is stationary.

4. An multi energy imaging system comprising:
a radiation source;
a radiation detector array having a plurality of detector rows;
a computer operationally coupled to said radiation source and said radiation detector, said computer configured to:
control the imaging system to acquire data from said radiation detector at a Z location with a first x-ray spectrum; and
control the imaging system to acquire data at the Z location from said radiation detector with a second x-ray spectrum different from the first x-ray spectrum, wherein the data acquired with the first x-ray spectrum and the data acquired with the second x-ray spectrum are acquired interleaved by different rows of the detector array; and said system further comprising a table and a data acquisition system (DAS) and said imaging system has a detector aperture of "d", and said computer further configured to control the imaging system to translate the table at "t" mm/s, to operate the DAS to sample at a rate of "s" Hz, and to alternate radiation potentials at a rate s=t/d so that a z-location is sampled by two different potentials by two detector rows used for data acquisition.

5. A system in accordance with claim 4 wherein said computer further configured to compute a basis material decomposition on the acquired data from the first x-ray spectrum and the second x-ray spectrum.

6. A system in accordance with claim 4 wherein said computer further configured to generate a difference image from the acquired data from the first x-ray spectrum and the second x-ray spectrum.

7. A system in accordance with claim 4 wherein said computer further configured to:
acquire data at a first angle at a Z location with a first x-ray spectrum;
acquire data at the first angle at the Z location with a second x-ray spectrum different from the first x-ray spectrum;
acquire data at a second angle at the Z location with the first x-ray spectrum; and
acquire data at the second angle at the Z location with the second x-ray spectrum different from the first x-ray spectrum.

8. A system in accordance with claim 7 wherein said computer further configured to generate a stereoscopic view using the acquired data from the first and second angles.

9. A system in accordance with claim 7 wherein said computer further configured to:
generate a first difference image from the acquired data from the first x-ray spectrum and the second x-ray spectrum at the first angle;
generate a second difference image from the acquired data from the first x-ray spectrum and the second x-ray spectrum at the second angle; and
generate a stereoscopic view using the first and second difference images.

10. A system in accordance with claim 7 wherein said system further comprises a rotatable gantry, said radiation source and said radiation detector array mounted on said gantry, said computer further configured to acquire data at a second angle at the Z location with a first x-ray spectrum by rotating said gantry.

11. A system in accordance with claim 7 wherein said computer further configured to acquire data at a second angle at the Z location with a first x-ray spectrum by:
energizing a first portion of said radiation source such that a first x-ray spectrum is emitted by said first portion; and
energizing a second portion of said radiation source such that a second x-ray spectrum different from the first spectrum is emitted by said second portion.

12. A system in accordance with claim 11 wherein said system further comprises a rotatable gantry, said radiation source and said radiation detector array mounted on said gantry, said computer configured to maintain said gantry stationary while acquiring the data.

13. A system in accordance with claim 4 wherein said computer further configured to modulate an x-ray tube voltage to generate the first and second x-ray spectrums.

14. An imaging system in accordance with claim 4 further comprising filters between said radiation source and said radiation detector array such that different detector rows collect projections of different x-ray energy spectra.

15. A mechanical computed tomographic (CT) imaging system comprising:
a rotatable gantry;
a x-ray source mounted on said gantry;
a x-ray detector comprising a plurality of detector rows mounted on said gantry substantially opposite said source; and
a computer operationally coupled to said gantry, said source, and said detector, said computer configured to:

control the CT imaging system to acquire scout data from said x-ray detector at a Z location with a first x-ray spectrum; and control the CT imaging system to acquire scout data at the Z location from said x-ray detector with a second x-ray spectrum different from the first x-ray spectrum, wherein the scout data acquired with the first x-ray spectrum and the scout data acquired with the second x-ray spectrum are acquired interleaved by different rows of the detector; and said system further comprising a table and a data acquisition system (DAS), said imaging system having a detector aperture of "d", and said computer further configured to control the imaging system to translate the table at "t" mm/s, to operate the DAS to sample at a rate of "s" Hz, and to alternate radiation potentials at a rate s=t/d so that a z-location is sampled by two different potentials by two detector rows used for data acquisition.

16. A system in accordance with claim 15 wherein said computer further configured to maintain said gantry stationary while acquiring the scout data.

17. An imaging system in accordance with claim 15 further comprising filters between said x-ray source and said x-ray detector such that different detector rows collect projections of different x-ray energy spectra.

18. A method for obtaining data, said method comprising:

operating a Computed Tomography (CT) imaging system comprising a detector array having a plurality of detector rows to acquire scout data at a Z location with a first x-ray spectrum;

operating the CT imaging system to acquire scout data at the Z location with a second x-ray spectrum different from the first x-ray spectrum; and performing a basis material decomposition on the acquired scout data from the first x-ray spectrum and the second x-ray spectrum;

wherein a detector aperture is "d" in mm, and the CT imaging system comprises an x-ray tube, a table, and a data acquisition system (DAS), and said method further comprises translating the table at "t" mm/s, operating the DAS to sample at a rate of "s" Hz, and alternating x-ray tube potentials at a rate s=t/d so that a z-location is sampled by two different potentials by two detector rows used for data acquisition.

19. A mechanical computed tomographic (CT) imaging system comprising:

a rotatable gantry;

a x-ray source mounted on said gantry;

a x-ray detector comprising a plurality of detector rows mounted on said gantry substantially opposite said source; and a computer operationally coupled to said gantry, said source, and said detector, said computer configured to:

operate the CT imaging system to acquire scout data at a Z location with a first x-ray spectrum;

operate the CT imaging system to acquire scout data at the Z location with a second x-ray spectrum different from the first x-ray spectrum; and perform a basis material decomposition on the acquired scout data from the first x-ray spectrum and the second x-ray spectrum;

wherein the scout data acquired with the first x-ray spectrum and the scout data acquired with the second x-ray spectrum are acquired interleaved by different rows of the detector and further wherein said acquiring scout data at a Z location with a first x-ray spectrum comprises acquiring scout data at a first angle at a Z location with a first x-ray spectrum, said acquiring scout data at the Z location with a second x-ray spectrum different from the first x-ray spectrum comprises acquiring scout data at the first angle at the Z location with a second x-ray spectrum different from the first x-ray spectrum, and said computer further configured to:

operate the CT imaging system to acquire scout data at a second angle at the Z location with a first x-ray spectrum;

operate the CT imaging system to acquire scout data at the second angle at the Z location with a second x-ray spectrum different from the first x-ray spectrum;

generate a first difference image from the acquired scout data from the first x-ray spectrum and the second x-ray spectrum at the first angle;

generate a second difference image from the acquired scout data from the first x-ray spectrum and the second x-ray spectrum at the second angle; and generate a stereoscopic view using the first and second difference images.

20. A system in accordance with claim 19 wherein to acquire scout data at a second angle at the Z location with a first x-ray spectrum, said computer further configured to operate the CT imaging system to acquire scout data at a second angle at the Z location with a first x-ray spectrum by rotating said gantry.

21. A system in accordance with claim 19 wherein to acquire scout data at a second angle at the Z location with a first x-ray spectrum said computer further configured to operate the CT imaging system to acquire scout data at a second angle at the Z location with a first x-ray spectrum by using a distributed x-ray source such that a gantry of an imaging system is stationary.

* * * * *